United States Patent [19]

Akinc et al.

[11] Patent Number: 5,002,399.

[45] Date of Patent: Mar. 26, 1991

[54] THERMOPOROSIMETER

[76] Inventors: Mufit Akinc, 4929 Utah Dr., Ames, Iowa 50010; Yuksel Sarikaya, 14th St., Apt. 29-7, Umut Apartments, Bahcelievler Ankara, Turkey

[21] Appl. No.: 356,748

[22] Filed: May 24, 1989

Related U.S. Application Data

[63] Continuation-in-part of Ser. No. 76,950, Jul. 23, 1987, abandoned.

[51] Int. Cl.⁵ ...................... G01N 15/08; G01N 25/56
[52] U.S. Cl. ........................................ 374/14; 374/45; 374/54; 73/38; 73/73
[58] Field of Search .................... 374/10–14, 374/16, 27, 45, 54; 73/38, 73, 76

[56] References Cited

U.S. PATENT DOCUMENTS

| | | | |
|---|---|---|---|
| 3,554,001 | 1/1971 | Norem | 374/14 |
| 3,902,354 | 9/1975 | Harlan et al. | 374/14 |
| 4,165,633 | 8/1979 | Raisanen | 73/76 |
| 4,316,384 | 2/1982 | Pommer et al. | 73/76 |
| 4,453,398 | 6/1984 | Demirel et al. | 374/45 |
| 4,489,593 | 12/1984 | Pieters et al. | 73/38 |
| 4,623,263 | 11/1986 | Barberi et al. | 73/38 |

OTHER PUBLICATIONS

Brun et al., "A New Method for the Simultaneous Determination of the Size and the Shape of Pores: The Thermoporometry," *Thermochimica Acta*, 21, 1977, pp. 59–88.

*Primary Examiner*—William A. Cuchlinski, Jr.
*Assistant Examiner*—William C. Dowling
*Attorney, Agent, or Firm*—Zarley, McKee, Thomte, Voorhees & Sease

[57] ABSTRACT

A thermoporosimeter for accurately and inexpensively determining porosity characteristics of material. The material is saturated with a liquid and then placed within an enclosed area and in communication with a mass measuring unit. A furnace with a furnace control provides increasing heat to the material within the enclosed area. As the liquid saturated in the pores of the material evaporates, the mass of the material changes and is recorded by the mass measuring unit. The mass measuring unit communicates the values for mass change through an interface to a microcomputer. A temperature sensor located within the enclosed area also provides temperature values to the computer through an interface. By measuring the change in mass as a function of temperature, it is possible to determine porosity characteristics of the material, which include but are not limited to, pore size, pore volume, and pore size distribution of the material.

13 Claims, 2 Drawing Sheets

THERMOPOROSIMETER

This is a continuation-in-part application generated from Ser. No. 76,950 filed July 23, 1987, and now abandoned entitled THERMOPOROSIMETER.

BACKGROUND OF THE INVENTION

This invention relates to an improved method of determining porosity characteristics of materials where the material to be studied is saturated with a liquid, subjected to a temperature increase whereby at least some liquid evaporates, and the resulting change in mass of the material is measured to analyze porosity of the material.

It is desirable to determine the porosity characteristics of certain materials since the extent of porosity influences other properties and assists in determining the usefulness of such materials. Porosity affects such things as the nature of strength, thermal and electrical conductibility, weatherability, permeability, and optical transparency of a material.

Some conventional methods used to determine porosity characteristics include electron microscopy, gas adsorption, mercury porosimetry, and phase transition porosimetry.

Electron microscopy involves direct observation of the pores of the material. While it is precise, it is not suitable for routine determination and rests upon the subjective determination of the operator of the instrument. It also has the disadvantage of involving the use of an expensive instrument to ascertain porosity.

Gas adsorption measures the size of pores by the adsorption and condensation of vapors in the pore space. Amount of vapor condensed in the pores at a given vapor pressure has been found to be related to pore volume, and pore size distribution is determined in this way. It has limited application, since it can be used only with material containing pores in the mesospore range of 3 nm (nanometer) to 50 nm. It is tedious, time consuming, and, as with electron microscopy, is also expensive to perform.

Use of a mercury porosimeter is one of the most frequently applied methods of determining porosity. Mercury is forced into the pores of the material and the volume of mercury which enters the pores is measured in relation to the pressure applied. The well-known Washburn equation, which can be found at S. Lowell, Introduction to Powder Surface Area, pgs 181–89 (Wiley & Sons, 1979), then allows the calculation of the pore size distribution, whereby pressure applied and pore radius are related. It can be effectively used with pore sizes between 4 nm to several micrometers. Some disadvantages with mercury porosimeters are discussed in U.S. Pat. No. 4,453,398, Demirel, et al., issued June 12, 1984 and relating to an ice porosimeter.

Among the disadvantages of mercury porosimetry are uncertainties in the relationship between pressure and pore radius. Certain empirical relationships are utilized; however, certain assumptions have to be made to arrive at results which are translated into porositic characteristics. Parameters such as pore cross-section geometry, surface tension of liquid in pores, and contact angles with regard to liquid and pores must be utilized in this method.

The Washburn equation assumes pores are cylindrical with perfectly circular cross-sections, while in nature this does not occur. Further, surface tension and contact angle values also vary in nature, while the equation presumes these to be constant. In addition, the material to be measured must be evacuated, and then pressurized, which can destroy the pore structure of the sample. The cost is relatively high and a concern exists about the health hazards of working with mercury.

Phase transition porosimetry, as described in U.S. Pat. No. 4,453,398, uses the change in volume of water in the pores as the same is frozen and/or thawed. The water-saturated sample is placed in mercury, and temperature and volume changes are measured as the material is frozen and/or melted. Pore water is expelled as the ice melts and changes in volume.

This device and process, while workable, can be effectively utilized only in material with pore size ranges of 2 nm to 100 nm, and is not suitable for use in measuring materials with large-size pores. The volume change is not large and is difficult to measure. This process also involves the use of the hazardous material mercury.

Accordingly, it is an object of the present invention to provide for determination of porosity characteristics of a material by measuring the change in mass of the material as liquid saturated in its pores evaporates.

A further objective of the invention is to provide for an accurate means of determining porosity characteristics of a material.

Another objective is to provide a means and method of determining porosity characteristics that does not require high pressures, evacuation or drying of the material which may destroy the pore structure.

Yet another objective is to provide a simpler and safer method of determining porosity characteristics which does not require high pressure or the use of hazardous vapors or materials.

Another objective is to provide a means of determining porosity characteristics of material which is rugged, efficient, and less expensive than other means, and which has wide ranging applicability to a variety of materials with a variety of different pore sizes, structures or shapes.

These and other objects, features, and advantages of the present invention will become apparent with reference to the accompanying specification and claims.

SUMMARY OF THE INVENTION

The invention utilizes a unit for recording mass, a heating assembly with a temperature sensor, and a microprocessor interfacing with the mass recording unit.

The material to be studied for pore size and characteristics is saturated with liquid and placed in operative communication with the mass recording unit. The material is then heated until at least some of the liquid evaporates. The change in mass is used with the correlated measurements of temperature change to determine pore characteristics of the material.

DETAILED DESCRIPTION OF THE PREFERRED EMBODIMENT

With reference to the drawings, a detailed description of the preferred embodiment of the invention will now be given. This description is set forth to aid in an understanding of the invention.

Figure 1:
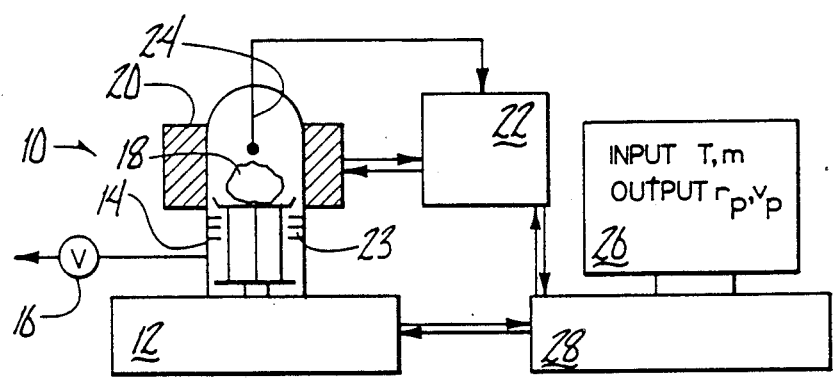
FIG. 1 is a schematic diagram of an embodiment of the invention.

FIG. 1 represents an embodiment of the invention adapted for determining porosity characteristics of relatively large samples or materials. The thermoporosimeter is generally represented at 10. It includes a balance 12 which, with larger objects, preferably involves a semi-microbalance with RS-232 output, an option allowing the balance to be interfaced with a microcomputer 26. A glass enclosure 14 sits on top of the balance 12 and has a restricted outlet 16. The sample material 18 to be measured is placed upon the balance 12. Balance 12 basically presents a sample chamber where the sample can be isolated for temperature and pressure control, and its mass can be continuously measured to high precision.

A tube furnace 20 surrounds the enclosure 14 and provides the temperature increase necessary to the invention. A furnace controller 22 determines the level and rise of temperature. Thermal barriers, represented at 23, assist in confining the temperature increase to the area surrounding the sample 18. A temperature sensor 24 is connected to the furnace controller 22 to control the ambient temperature around the sample 18 and to provide temperature readings.

A microcomputer is provided at 26 which includes an interface 28 with the temperature sensor 24 (through controller 22) and balance 12. In addition to compiling readings from the temperature sensor 24 and balance 12, it performs the necessary calculations to derive porosity characteristics from the readings. Microcomputer 26 also can be utilized for process control. It can supervise the procedure to insure that the data being obtained is correlated, and to somewhat automate the analytical procedure.

While FIG. 1 represents a schematic diagram of a preferred thermoporosimeter for larger samples, the specific hardware for each of the semi-microbalance 12, temperature sensor 24, tube furnace 20, and microcomputer 26 are not critical, as such devices are individually known and available from instrument suppliers of balances such as Fischer Instruments or Cole-Parmer; suppliers of temperature sensors such as Omega Co. or Eurotherm; ceramic furnace manufacturers including Zircar Products, Inc.; and microcomputer suppliers, for example, IBM and Zenith.

Figure 2:
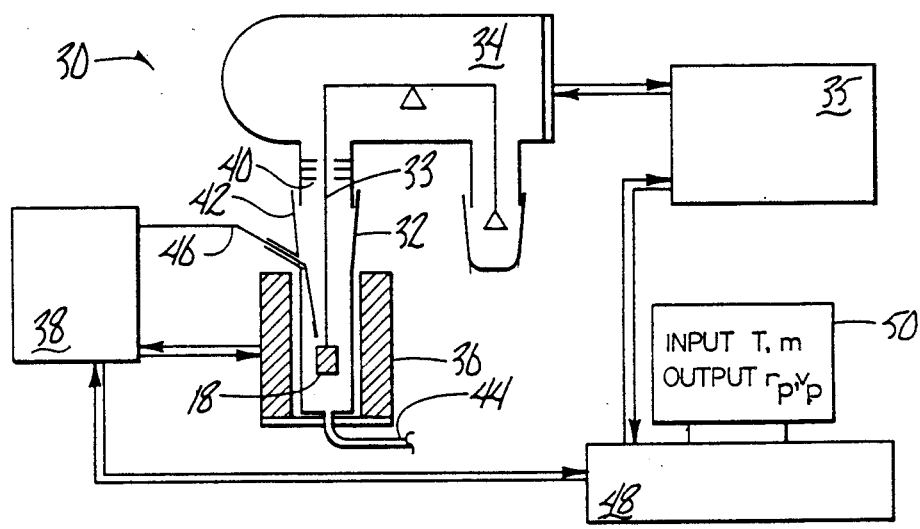
FIG. 2 is a schematic diagram of a second embodiment of the invention.

A second embodiment, shown at FIG. 2, is designed for measuring the porosity of smaller samples. The thermoporosimeter represented at 30 involves placement of the sample 18 within an enclosure 32. It is connected by a PTFE (polytetrafluoroethylene or TEFLON ® brand name) hangdown wire 33 to a balance 34 sensitive to micrograms. Controls and readings of balance 34 are provided at balance control 35. A tube furnace 36 surrounds the enclosure 32 and is connected to furnace controls 38. Thermal and vapor barriers are provided at 40. A vapor outlet 42 and vapor inlet 44 assist in controlling conditions within enclosure 32.

A temperature sensor 46 is also connected to the furnace controller 38, and which in turn at the interface 48, connects to the microcomputer 50 to provide temperature readings to computer 50. The balance 34 also provides readings to the microcomputer 50 through balance control 35 and interface 48.

The materials used for the various components should be corrosion resistant, since the sample 18 will be saturated with liquid in the process. Suitable individual pieces of apparatus for assembly in use with the small pore determining unit can be as previously described.

The first embodiment involves adaptation of the device to measuring relatively large materials and includes a top-loading balance to measure mass changes. The second embodiment necessarily involves adaptations for measuring smaller materials and relatively smaller changes in mass. A more sensitive balance is provided for and thermal barriers are more restrictive, with more barriers and a smaller opening. It is necessary to keep as much heat as possible away from the microbalance, since it is very sensitive. A hangdown wire is also necessitated in adapting the balance to measure small mass changes.

In operation, the measurement of porosity characteristics of a larger sample (FIG. 1) is made by first saturating the sample 18 with a liquid, in this example, water. The material is then placed on the balance 12, and the controller 22 is used to cause tube furnace 20 to increase the temperature inside the enclosure 14 surrounding the sample 18. With the sample saturated with water, the tube furnace 20 is used to increase the temperature to 100° C., the boiling point of water. Water in the pores begins to evaporate. The water continues to evaporate up to 350° C. because water in some of the pores will have a higher boiling point caused by different reductions of vapor pressure over the concave meniscus for different sized pores, as will be discussed in more detail later. The balance 12 measures the changing mass of the sample 18 and communicates this information through interface 28 to the microcomputer 26. The temperature sensor 24 also communicates temperature information through the interface 28 to the microcomputer 26. The computer provides calculations to relate the changing mass of the sample to the changing temperature.

It can thus be seen that these described embodiments according to the invention provide a method and specific apparatus for deriving porosity characteristics of various sample materials which achieves at least all of the stated objectives of the invention. The information regarding change in temperature and change in mass of the sample during the procedure can be communicated to a computing means such as computer 26 in FIG. 1 or computer 50 in FIG. 2. These measurements then provide the basis for calculating and deriving the particular porosity characteristics from known empirical relationships, such as are well known to those skilled in the art. The computer enables the final results to be derived quickly, repetitively, and efficiently. The results can also be stored, displayed, and correlated, functions of computers which are widely appreciated in the art.

Empirical relationships are utilized in other pore symmetry methods to estimate and model the porosity characteristics of materials. For example, in the Demirel U.S. Pat. No. 4,453,398, issued June 12, 1984, previously referenced, known relationships between such things as the melting point of ice and the radius of pores can be expressed mathematically (see equation (1) column 3, line 62 of Demirel). The Demirel patent teaches that monitoring temperature and volume changes of a sample initially saturated with water which is frozen, porosity characteristics such as pore-size distribution, pore volume, and specific surface of the sample material, can be derived, as discussed at columns 4 and 5 of Demirel, and exemplified by the various equations and mathematical calculations.

By way of another example, known empirical relationships exist in mercury porosimetry. For example in the article entitled "Evaluation of Hysteresis in Mercury Intrusion Porosimetry by Second-Intrusion Method" by Cebeci, et al., from Transportation Research Record 675, 1978, the mathematical relationship between intrusion pressure and pore radius (called the Washburn equation) is set forth. This equation is utilized to derive porosity characteristics by the measurements obtained in mercury porosimetry.

Similarly, in the present invention, the techniques of the embodiment shown in FIG. 1 are utilized to derive the temperature and mass change data. This data is then utilized in known empirical formulas and relationships, and combined with other known or derivable information to perform known mathematical calculations which ultimately lead to results which can be utilized to model or estimate porosity characteristics of a sample.

For a better understanding of the present invention, the following are some examples of the empirical relationships and calculations which can be utilized with the present invention to derive porosity characteristics. For example, it is known that a meniscus forms at the top of fluid within a pore (such as is diagrammatically depicted in FIG. 3). It is also known that liquid within a pore having a meniscus does not evaporate as readily as liquid having a flat upper surface. See for example Allen, "Particle Size Measurement" John Wiley & Sons, New York 1974, Chapter 18, Section 18.2, page 414. This is because there is a lower vapor pressure over a concave meniscus then a flat surface.

Figure 3:
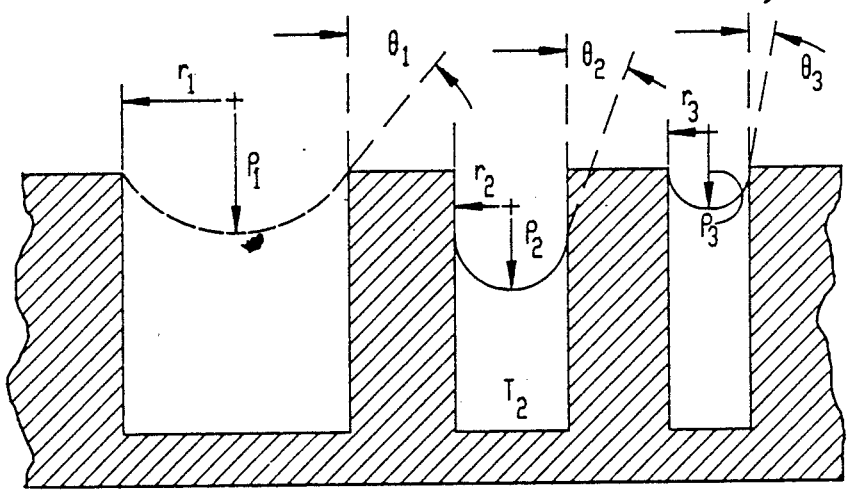
FIG. 3 is a schematic representation of the relationship of pore size to evaporation of liquid from a pore, and includes a showing of how pore diameter relates to surface tension and contact angle between liquid and pore.

Therefore, the boiling temperature of liquid in a pore is raised because of reduction of vapor pressure over a concave meniscus. FIG. 3 diagrammatically depicts how different pore sizes cause differently shaped meniscus for liquid within those pores.

In FIG. 3, $r_1$, $r_2$, and $r_3$ indicate the radius of each of the different diameter pores shown largest to smallest from left to right. $\rho_1$, $\rho_2$, and $\rho_3$ represent the radius of curvature of the meniscus for each pore respectively. Angles $\theta_1$, $\theta_2$, and $\theta_3$ refer to the contact angle of the meniscus with the walls of each respective pore. Such is well known as is disclosed in Moore, Physical Chemistry, Prentis-Hall, Englewood Cliffs, N.J. (Chapter 11, page 480, 4th Edition). The extent of boiling point elevation is related to radius of the curvature; because of different vapor pressures over the differently shaped meniscus. The smaller the radius of curvature, the higher the boiling temperature. Therefore, upon heating, the liquid in the largest pores evaporates first, followed by evaporation in smaller pores.

Evaporation of liquid from a pore system, which originally had all pores basically saturated or filled, is diagrammatically illustrated in FIG. 3. At temperature $T_2$, the pore with $r_1$ is already emptied, $r_2$ is being emptied, and $r_3$ is still full.

The above relationships are then useful with the following mathematics, for example, to derive porosity characteristics about a material. The invention, again, is utilized to obtain data regarding temperature and mass changes which are combined with calculations such as follows to obtain meaningful and accurate information regarding the porosity of material.

In the following equations, P refers to the pressure; r=pore radius; $T_o$ and T represent bulk and capillary boiling temperatures, respectively; $\Delta H_V$ refers to molar enthalpy for vaporization; V refers to molar volume; $\gamma$ refers to surface tension; P refers to radius of curvature; and subscripts s, l, and g refer to solid, liquid, and gas, respectively.

It is well known to those skilled in the art that evaporation of liquid at equilibrium can be expressed as:

$$-S_l dT + V_l dP_l = -S_g dT + V_g dP_g \tag{1}$$

where $S_l$ and $S_g$ refer to entropy of the liquid and gas phase, and dT and dP refer to infinitesimal change in the temperature and the pressure respectively. Also, at constant liquid pressure, the following are satisfied:

$$dP_l = 0, P_g = P_l + \frac{2\gamma_{lg}}{P_{lg}}, dP_g = d\left(\frac{2\gamma_{lg}}{r_{lg}}\right) \tag{2}$$

The equilibrium condition also provides:

$$\Delta H_v = T(S_g - S_l) \tag{3}$$

Equations 1-3 are conventional and well known in the art fundamental relationships, which have been commonly known for many years. These relationships can be found in generally available texts, in treatises, and are well known to those skilled in the art.

Substituting the expression in equation 3 into equation 1 and assuming $V_g > V_l$, one gets:

$$\frac{\Delta H_v}{T} dT = V_g dP_g \tag{4}$$

If the gas is ideal (assuming $V_g = RT/P_g$, where R is the universal gas constant, T is temperature and $P_g$ is the gas pressure as is a well-known ideal gas law, see for example, Moore, Physical Chemistry, supra, Chapter 6, Section 9, page 212, line 17, which is incorporated by reference) and by substituting the values of $P_g$ and $dP_g$ from equation (2), the expression becomes:

$$\frac{\Delta H_v}{T} dT = \frac{RT}{P_g} dP_g = RT \frac{d(2\gamma_{lg}/P_{lg})}{P_l + \frac{2\gamma_{lg}}{P_{lg}}} \tag{5}$$

and by dividing both sides of equation (5) with T and noting that $dx/x = d\ln x$ (commonly known in the art, see e.g. Moore, supra, Chapter 6, Section 9, page 212, equation (6.22));

$$\frac{\Delta H_v}{T^2} dT = R d\ln[(2\gamma_{lg}/P_{lg}) + P_l)] \tag{5.1}$$

These equations are well known in the art as shown by reference to Lupis, "Chemical Thermal Dynamics of Materials," Chapter XIII, pages 364-5 (North Holland 1983) which is incorporated by reference. The enthalpy of vaporization above normal boiling temperature is known as:

$$\Delta H_v = A + BT + CT^2 + DT^3 + ET^4 \tag{6}$$

This relationship is also well known in the art. See for example, Moore, supra, Chapter 2, Section 20, page 68, equation (2.42).

Substitution of equation (6) in equation (5.1) reveals the formula to be used in computing the pore dimensions. As can be seen, the right side of equation (6) is substituted for $\Delta H_v$ in equation (5.1). The resulting equation is simplified on both sides and integrated to produce equation (7);

$$A\left(\frac{1}{T_o} - \frac{1}{T}\right) + B\ln\frac{T}{T_o} + C(T - T_o) + \frac{D}{2}(T^2 - T_o^2) + \frac{E}{3}(T^3 - T_o^3) = R\ln\left(\frac{2\gamma}{P_p} + 1\right) \quad (7)$$

This relationship is also known in the art, see Lupis, supra, at page 364. $T_o$ and $T$ correspond to bulk and capillary boiling temperatures, and coefficients A, B, C, D, and E are available for most liquids. Such coefficients can be derived, as is well-known in the art, from standard and established references. For example, coefficients and variables for water can be derived by those of ordinary skill in the art from such texts as "CRC Handbook of Chemistry and Physics," (CRC Press, Inc., 60th Edition, 1979–80), page D-175; and Moore, supra, Chapter 6, Section 9, page 213 (Prentis-Hall, Inc., 1972). Moore, supra, at Chapter 2, Section 20, pages 67–68 directly describes and defines such coefficients, how they are computed, and gives specific examples of values for a variety of gases such as hydrogen, oxygen, water, etc. Moore, supra, at Chapter 2, Section 20, pages 67–68 states these values can be obtained from known enthalpy of vaporization versus temperature data, for example, as set forth in the CRC Handbook referenced above. Thus, equation 7 provides the desired relationship between boiling temperature of a liquid in a capillary and radius of curvature of the liquid in that capillary. It is further well known in the art and widely available in texts and treatises that the pore radius and curvature of liquid in a capillary is related by $\cos\theta = r/\rho$, where $\theta$ is the contact angle between liquid and solid, r is radius of the pore capillary, and $\rho$ is the radius of curvature of the liquid in the capillary. See, for example, Gregg and Sing, "Adsorption, Surface Area and Porosity," pages 122–123 (Academic Press 1982); and Moore, supra, at page 480, Chapter 11, both which are incorporated by reference.

Figure 4:
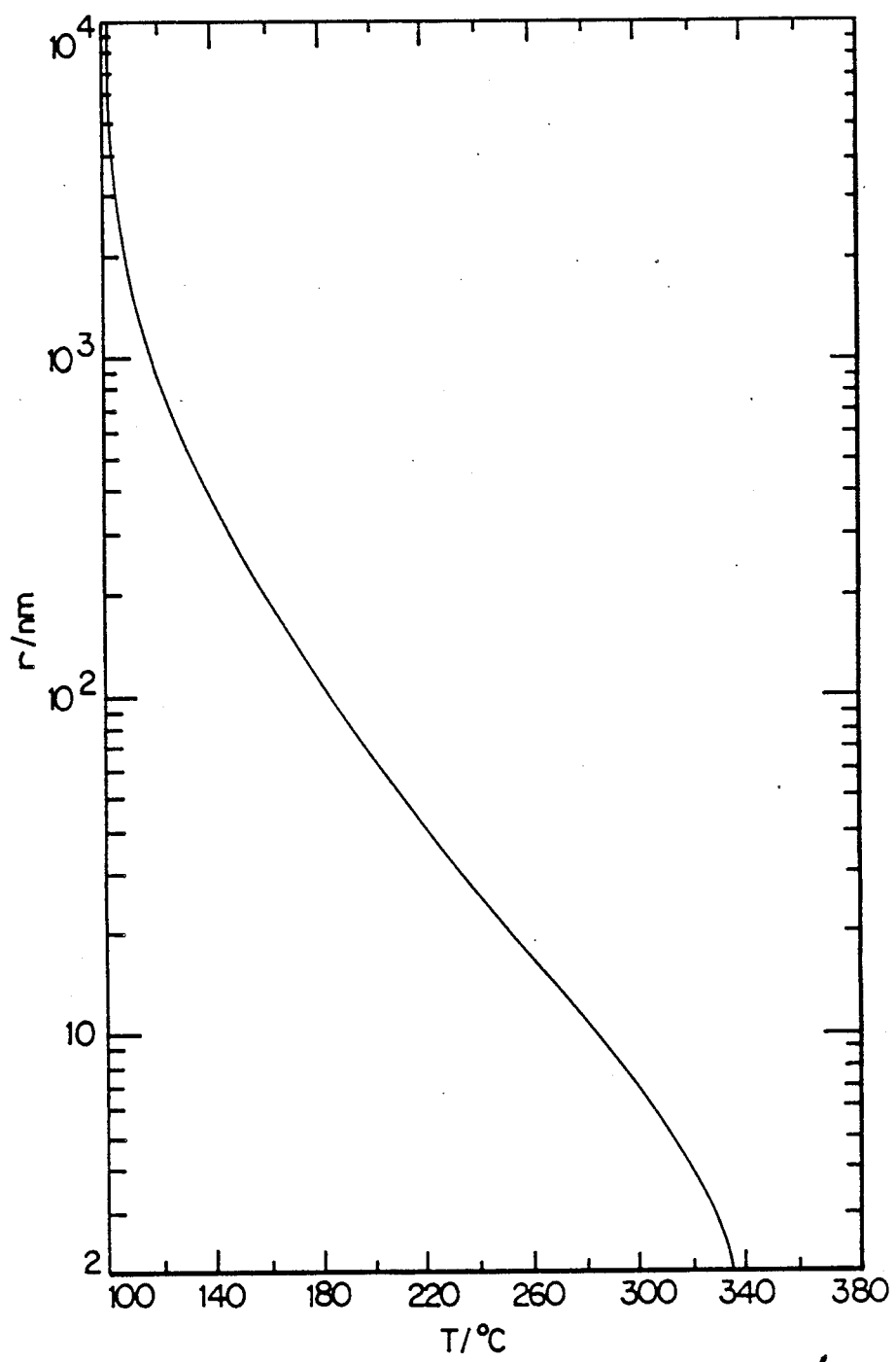
FIG. 4 is a graph of boiling temperature of water as a function of pore radius.

By way of application to the example, water at constant liquid pressure of one atmosphere and for $\theta = 0$ (where $\theta$ is the contact angle and pore radius is given by $r = \rho \cos\theta$), one gets:

$$11748\left(\frac{1}{T_o} - \frac{1}{T}\right) - 436.67 \ln\frac{T}{T_o} + 0.9552(T - T_o) - 4.0 \times 10^{-4}(T^2 - T_o^2) - 2.349 \times 10^{-8}(T^3 - T_o^3) = 8.314 \ln\frac{(1.9734 \times 10^{-4})\gamma}{r} + 1 \quad (8)$$

Where $T_o$ is 373.15° K. and $\gamma$ is the surface tension of water at temperature T. FIG. 4 shows plotting of boiling temperature as a function of pore radius for water. Using equation 8, surface tension and enthalpy of vaporization are assumed to be equal to their bulk values in constructing the r-T plot.

This shows that the relationships that can be derived from measuring values of temperature change as it relates to mass change in the material occurring as the liquid evaporates. Equation (8) is applied which relates temperature values to radius of the pore. Measured mass is then compared to pore radius and thus the pore size distribution can be derived.

The relationship between pore size and pore-size distribution is well known in the art. Standard texts such as Gregg and Sing, supra, as with most references dealing with porosity, set forth this type of relationship. It has been shown that the invention utilizes and records the mass of the sample ($M_s$) in correspondence to temperature ($T_s$). By subtraction of dry mass of the sample ($M_d$) for mass at a certain temperature, the mass of water ($M_w$) contained in the pores of the sample at that temperature is determined. A plot of mass of water versus temperature can be made. By using equation (8), temperature is converted to pore radius which can also be plotted. From this point there are numerous well known in the art ways to express pore-size characteristics and pore-size distribution. See for example, Lowell, *Introduction to Powder Surface Area*, Chapter 11, (John Wiley & Sons, N.Y., 1979). Chapter 11 is entitled "Mercury Porosimetry" and discusses these characteristics generally. Also, it is common knowledge in the art as to how different pore-size distribution characteristics are actually obtained. Cumulative pore-size distribution can be obtained by converting mass data to volume (volume = mass/density). Frequency distribution of pores of a certain volume and pore radius can be obtained by plotting consecutive volume values against pore radius. Normalized frequency distribution is obtained by dividing volume values by corresponding radius values and plotting the results against pore radius. These are but a few of the characteristics possible by obtaining data using the present invention, and are simply well known manipulations of the data.

Although water has been used as the liquid in the example, other liquids, both at room temperature and elevated temperatures, may be used where the physical and chemical properties are accurately known. Other suitable liquids include alcohols such as methyl alcohol, ethyl alcohol, isopropyl and organic liquids (including but not limited to $C_1$ to $C_3$ straight or branched chain alcohol) such as toluene, benzene and hexane. The principles used in deriving evaporation thermoporosimetry expressions are applicable to any liquid as long as no chemical reaction occurs between the liquid and solid phase. In other words, they are inert with respect to each other.

This technique may also be used to study the properties of the probe liquid as opposed to the sample porous material. When the pore size distribution of a solid is accurately determined by water evaporation, or with other techniques, then the solid may be used to determine the variation of surface tension of the liquid as a function of temperature or, in a similar manner, determine the enthalpy of evaporation as a function of temperature where one of the parameters of equation 7 is known.

The included preferred embodiment is given by way of example only, and not by way of limitation to the invention, which is solely described by the claims herein. Variations obvious to one skilled in the art will be included within the invention defined by the claims.

We claim:

1. A thermoporosimeter for deriving porosity measurements of liquid-saturated materials comprising: a mass recording unit for measuring mass changes of said materials as temperature changes; a heating means for increasing temperature of said materials
a means for measuring instantaneous temperature changes of said materials caused by said heating means associated with said thermoporosimeter; and
an operatively associated means for deriving the volume of pores and pore size distribution of said materials from the measurements from said mass recording unit as a function of the corresponding measurements from said means for measuring instantaneous temperature changes.

2. The device of claim 1, wherein said mass recording unit comprises a sensitive balance.

3. The device of claim 2, wherein said sensitive balance comprises a semi-microbalance with RS-232 output.

4. The device of claim 1, wherein said heating means comprises a tube furnace.

5. A method of determining pore size characteristics, pore volume, and pore size distribution of porous material comprising:
saturating said porous material with a liquid;
heating said saturated porous material to increasing temperatures which eventually exceed the heat of evaporation of said liquid;
measuring the changes in mass of said saturated porous material as a function of temperature; and
determining pore size characteristics, pore volume, and pore size distribution by relating the measurements of said mass change as a function of temperature to radius of pore as a function of temperature.

6. The method of claim 5, wherein said measurements are taken after said temperature has increased to where said liquid evaporates.

7. The method of claim 5, wherein said liquid is inert with respect to said porous material.

8. The method of claim 7, wherein said liquid is water.

9. The method of claim 8 wherein said temperature is increased to 100° C.

10. The method of claim 5, wherein said temperature is increased to a range of 25° C. to 350° C.

11. The method of claim 5, wherein said liquid is an alcohol.

12. The method of claim 11, wherein said liquid is a $C_1$ to $C_3$ straight or branched chain alcohol.

13. The method of claim 5, wherein said liquid is selected from the group of toluene, benzene or hexane.

* * * * *